US00PP14376P29

(12) United States Plant Patent
Takeuchi

(10) Patent No.: US PP14,376 P2
(45) Date of Patent: Dec. 16, 2003

(54) GROUNDCOVER ROSE PLANT NAMED 'KEISHUTOUPI'

(50) Latin Name: *Rosa hybrida*
Varietal Denomination: KEIshutoupi

(75) Inventor: Shunsuke Takeuchi, Kozaki-machi (JP)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/202,229

(22) Filed: Jul. 22, 2002

(51) Int. Cl.[7] ..... A01H 5/00
(52) U.S. Cl. ..... Plt./102
(58) Field of Search ..... Plt./102

*Primary Examiner*—Bruce R. Campell
*Assistant Examiner*—Annette Para
(74) *Attorney, Agent, or Firm*—Klarquist Sparkman LLP

(57) ABSTRACT

Groundcover rose plant having disease resistance, a compact plant habit and good for pot planting.

1 Drawing Sheet

Genus and species: *Rosa hybrida.*
Variety denomination: KEIshutoupi.

SUMMARY OF THE INVENTION

The present invention relates to a new and distinct variety of groundcover rose plant named KEIshutoupi which was originated by me by crossing the variety KORsami (not patented), with an unnamed seedling.

BACKGROUND OF THE INVENTION

The primary objective of this breeding was to produce a new rose variety having disease resistance, a compact plant but spreading habit, and good for planting in large containers.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Originality of flower color, being purplish pink with pinkish white centers;
2. Originality of flower shape, single and small;
3. Compact but spreading habit.

Asexual reproduction of this new variety by budding, as performed in Japan and Somis, Calif., shows that the foregoing and all other characteristics and distinctions come true to form and are established and transmitted through succeeding propagations.

COMPARISON WITH PARENTS

KEIshutoupi has a different flower color and also has a more flat, spreading plant habit than either parent.

COMPARISON WITH SIMILAR VARIETY

It differs from KORconta (U.S. Plant Pat. No. 10,637) in that KEIshutoupi has smaller flowers and foliage and is lower growing.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:
*Seed parent.*—KORsami (unpatented).
*Pollen parent.*—Unnamed seedling.

FLOWER

Observations made from plants beginning at one year of age grown in a garden environment at Somis, Calif., January, 2001–November 2001.

Blooming habit: Continuous.
Bud:
*Size.*—About 10–14 mm long when the petals start to unfurl.
*Form.*—The bud form is very long and very slender.
*Color.*—When sepals first divide, bud color is Red Group 55D with Red Group 55C on petal margins. When half blown, the upper sides of the petals are Red Group 55C; and the lower sides of the petals are Red Group 55D with Red Group 55C on margins.
*Sepals.*—Color: Upper surface: Green Group 138B with Yellow-Green Group 145C on outer edges. Lower surface: Yellow-Green Group 144A with Yellow-Green Group 145C on outer edges. Length: 10–12 mm. Width: 4–5 mm. Shape: Subulate. Surface texture: Upper: Hoary; Lower: Smooth. There are three lightly appendaged sepals. There are two unappendaged sepals with hairy edges.

*Receptacle.*—Color: Yellow-Green Group 144A. Shape: Apple. Size: Medium, about 3–4 mm long× 2–3 mm wide. Surface: Smooth.

*Peduncle.*—Length: Medium, averaging about 20–30 mm. Surface: Prickly, glandular. Color: Yellow-Green Group 144B. Strength: Erect, slender.

Bloom:

*Size.*—Small. Average open size is about 25–35 mm.

*Borne.*—In pyramidal clusters of 20–30 blooms.

*Stems.*—Strength: Normal. Average length is about 30–40 cm.

*Form.*—When first open: Bloom is flat. Permanence: Retains its form to the end.

*Petalage.*—Number of petals under normal conditions: 5–7.

*Color.*—The principal portions of the upper sides of the petals are Red Group 55C, the base portion being Yellow-White Group 158D, which color occasionally extents to the outer edge of the petals. The reverse sides of the petals are between Red Group 55C and Red Group 55D. Each petal has a Yellow Group 4C spot at its very base. The major color on the upper side is Red Group 55C.

*Variegations.*—None.

*Discoloration.*—The general tonality at the end of the first day: Red Group 55C. At the end of the third day: Red Group 55C. Petals fade to Red Group 55D by day 7, then drop.

*Fragrance.*—None.

Petals:

*Texture.*—Thin.

*Shape.*—Obovate.

*Margin.*—Entire.

*Apex shape.*—Obcordate.

*Base shape.*—Cuneate.

*Form.*—Flat.

*Arrangement.*—Informal.

*Petaloids.*—Number: Petaloids in the center are few to none, usually none. Color: Red Group 55C.

*Persistence.*—Petals drop off cleanly before drying.

*Lastingness.*—On the plant: Long (about 7–9 days). As a cut flower: Long (about 9–11 days).

Reproductive parts:

*Stamens.*—Number: 100–120. Anthers: Length: 0.5–1.0 mm. Color: Orange Group 24A. Arrangement: Regular around styles. Filaments: Color: Yellow Group 10B. Length: 4–6 mm. Pollen: Color: Orange Group 26A.

*Pistils.*—Number: 40–60. Styles: Color: Yellow-Green Group 149C. Length: 2–4 mm. Stigmas: Color: Yellow Group 13C. Length: 1 mm.

*Hips.*—None observed.

PLANT

*Form.*—Shrub.

*Growth.*—Very vigorous.

*Mature plant.*—Height: 40 cm at two years of age. Width: 100–140 cm

*Rootstock.*—Dr. Huey.

Foliage: Number of leaflets on normal mid-stem leaves: 5–7.

*Size.*—Length: 45–50 mm. Width: 22–25 mm.

*Quantity.*—Abundant.

*Color.*—New foliage: Upper side: Between Yellow-Green Group 144A and Green Group 143A with Greyed-Purple Group 187B on margins. Lower side: Yellow-Green Group 146C. Old foliage: Upper side: Green Group 137A. Lower side: Yellow-Green Group 146B.

Leaflets:

*Size.*—Small (10–15 mm long×6–9 mm wide).

*Shape.*—Ovate.

*Base shape.*—Obtuse.

*Apex shape.*—Acute.

*Texture.*—Very glossy.

*Edge.*—Serrated.

*Serrations.*—Single, small.

*Petiole.*—Color: Yellow-Green Group 145B.

*Petiole rachis.*—Color: Yellow-Green Group 144A. Underside: Prickles and glands.

*Stipules.*—Short (about 8–10 mm long.)

*Disease resistance.*—Resistant to mildew, blackspot and rust under normal growing conditions.

*Pest persistence.*—Not tested.

*Vein color.*—Yellow-Green Group 145B.

*Venation pattern.*—Reticulate.

Wood:

*New wood.*—Color: Greyed-Red Group 181A and Yellow-Green Group 146C. Bark: Smooth.

*Old wood.*—Color: Yellow-Green Group 144A. Bark: Smooth.

Prickles:

*Quantity.*—On main canes from base: 15–20 per 16 cm.

*Form.*—Hooked downward.

*Length.*—6–8 mm.

*Color when young.*—Greyed-Purple Group 184C.

*Color when mature.*—Greyed-Orange Group 163D.

Small prickles:

*Quantity.*—On main stalks: None. On laterals: Few.

*Color.*—Greyed-Purple Group 184C.

Winter hardiness: Hardy to Zone 5.

I claim:

1. A new and distinct variety of rose plant of the ground-cover class, substantially as herein shown and described, characterized particularly by having disease resistance, a compact plant habit and being good for pot planting.

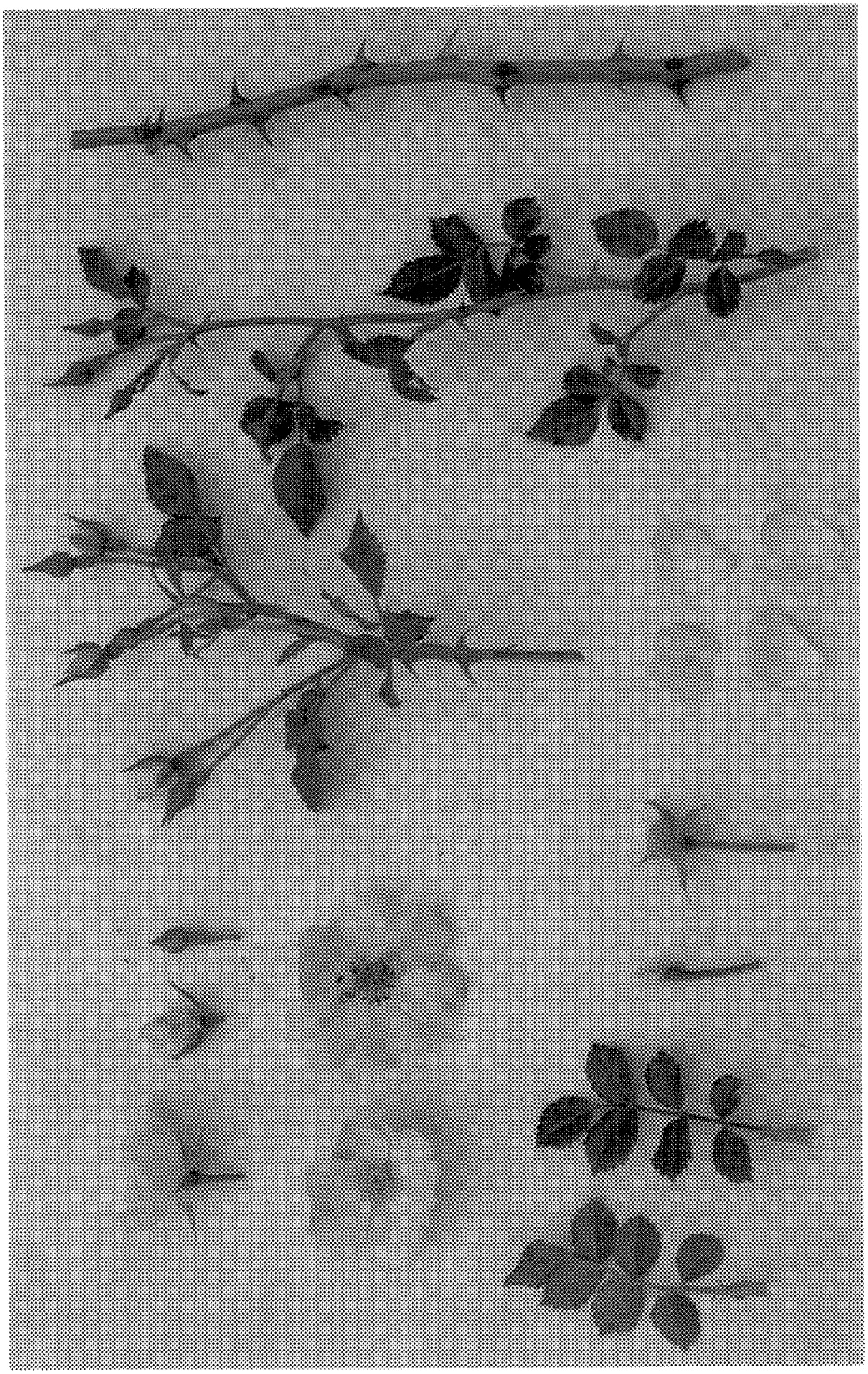

* * * * *